(12) United States Patent
Bacher et al.

(10) Patent No.: US 7,879,060 B2
(45) Date of Patent: Feb. 1, 2011

(54) BALLOON TREPAN

(75) Inventors: Uwe Bacher, Tuttlingen (DE); Michael Sauer, Tuttlingen (DE); Martin Oberlaender, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 861 days.

(21) Appl. No.: 11/135,531

(22) Filed: May 23, 2005

(65) Prior Publication Data

US 2005/0261724 A1    Nov. 24, 2005

Related U.S. Application Data

(63) Continuation of application No. PCT/EP03/12959, filed on Nov. 19, 2003.

(30) Foreign Application Priority Data

Nov. 22, 2002  (DE)  .............................. 102 54 503

(51) Int. Cl.
    A61M 29/00        (2006.01)
(52) U.S. Cl. ..................................... 606/192
(58) Field of Classification Search .............. 606/1,
    606/190, 191, 192; 604/96.01, 104, 178,
    604/105, 106, 107, 108
    See application file for complete search history.

(56) References Cited

U.S. PATENT DOCUMENTS

| 4,976,710 | A |   | 12/1990 | Mackin ........................ 606/15 |
|-----------|---|---|---------|--------------------------------------|
| 5,029,574 | A |   | 7/1991  | Shimamura et al. ............ 128/6   |
| 5,188,630 | A |   | 2/1993  | Christoudias ................... 606/1 |
| 5,540,711 | A | * | 7/1996  | Kieturakis et al. .......... 606/192  |
| 5,601,589 | A | * | 2/1997  | Fogarty et al. .............. 606/192 |
| 5,607,443 | A | * | 3/1997  | Kieturakis et al. .......... 606/192  |
| 5,632,761 | A | * | 5/1997  | Smith et al. ................. 606/192 |
| 5,730,756 | A | * | 3/1998  | Kieturakis et al. .......... 606/190  |
| 5,779,728 | A | * | 7/1998  | Lunsford et al. ............ 606/190  |

(Continued)

FOREIGN PATENT DOCUMENTS

DE    38 88 829 T2    12/1989

(Continued)

OTHER PUBLICATIONS

International Search Report; Mar. 2, 2004.

*Primary Examiner*—Gary Jackson
*Assistant Examiner*—Tuan V Nguyen
(74) *Attorney, Agent, or Firm*—St. Onge Steward Johnston & Reens LLC (57) ABSTRACT

The balloon trepan is used in minimal invasive surgery in order to create or maintain the area required for an operation by dilation of tissue or dissection of layers of tissue. The connection between the balloon and the sleeve of the trepan must be easily and securely produced without enlarging the outer diameter of the balloon trepan. The balloon must be secured against slipping and must be able to resist pressure during inflation. The balloon surrounding the distal end of the trepan is pressed against a peripheral step formed on the sleeve of the trepan by a clamping element in order to fix it to the sleeve of the trepan. The clamping element is displaced by rotation of at least one part of the clamping element about a longitudinal axis of the sleeve of the trepan in a longitudinal direction in relation to the said sleeve.

17 Claims, 7 Drawing Sheets

U.S. PATENT DOCUMENTS

| | | | | |
|---|---|---|---|---|
| 5,860,997 A | * | 1/1999 | Bonutti | 606/190 |
| 5,868,662 A | | 2/1999 | Borodulin et al. | 600/105 |
| 5,925,058 A | | 7/1999 | Smith et al. | 606/190 |
| 6,142,945 A | | 11/2000 | Sakamoto et al. | 600/459 |
| 6,352,544 B1 | * | 3/2002 | Spitz | 606/159 |
| 6,908,454 B2 | * | 6/2005 | McFarlane | 604/178 |

FOREIGN PATENT DOCUMENTS

| | | |
|---|---|---|
| DE | 696 10 080 T2 | 8/2000 |

* cited by examiner

Fig. 1

Fig. 2 ts of the outer sleeve is reduced by the step in the direction of its distal aperture. The balloon end is at first pressed around the outside of this step. In the next phase the balloon end is fixed by inserting the inner sleeve into the outer sleeve. On the outside of the inner sleeve a step is formed, which presses the balloon end against the inner step of the outer sleeve.

BALLOON TREPAN

This application is a continuation of pending International Patent Application No. PCT/EP2003/012959 filed Nov. 19, 2003, which designates the United States and claims priority of pending German Application No. 102 54 503.0 filed Nov. 22, 2002.

FIELD OF THE INVENTION

The balloon trepan is used in minimally invasive surgery in order to create or maintain the area required for an operation by dilation of tissue or dissection of layers of tissue. The connection between the balloon and the sleeve of the trepan must be easily and securely produced without enlarging the outer diameter of the balloon trepan. The balloon must be secured against slipping and must be able to resist pressure during inflation. The balloon (11, 12) surrounding the distal end of the trepan (15, 16) is pressed against a peripheral step (66, 95) formed on the sleeve (15, 16) of the trepan by means of a clamping element (18, 102) in order to fix it to the sleeve (15, 16) of the trepan. The clamping element (18, 102) is displaced by rotation of at last one part of the clamping element (18, 102) about a longitudinal axis of the sleeve (15, 16) of the trepan in a longitudinal direction in relation to the said sleeve (15, 16).

DESCRIPTION OF THE INVENTION

The invention relates to a balloon trepan consisting of a trepan sleeve and a balloon which can surround a distal end of the trepan sleeve, and the balloon can be pressed against a peripheral step formed on the sleeve of the trepan by means of a clamping element in order to fix it to the sleeve of the trepan. A balloon trepan of this kind is described, for instance, in the U.S. Pat. No. 5,607,443.

Instruments of the kind serve to create or to maintain an area required for an operation by dilation of tissue or dissection of layers of tissue.

The instrument along with balloon is referred to in the present document as a balloon trepan, while the instrument without balloon is called the sleeve of the trepan.

In minimally invasive surgery technology that is the basis for using balloon trepans, the balloon trepan is introduced into the body cavity by means of an incision. The size of this incision is chosen to be large enough so that the distal end of the sleeve of the trepan can be inserted while surrounded by the balloon in non-inflated condition. After positioning the balloon trepan at the desired spot in the body cavity, the tissue can be dilated or dissected by inflating the balloon with a gas such as air or carbon dioxide, or a liquid such as water.

By means of the sleeve of the trepan, an endoscope can be inserted. In using a balloon that is at least partly made of transparent material, the operating area can be observed.

Balloon trepans are used, for instance, in dilating the extraperitoneal area in hernia operations.

The balloon used can be made of stretchable materials. Silicone, for instance, has proven suitable. Appropriate balloons are shaped in such a way that they can be folded and secured over the distal end of the sleeve of the trepan. During inflation the balloon is enlarged by stretching the elastic material.

Balloons of inelastic material are also used. With these types of balloon the shape of the balloon in inflated condition is already determined. To introduce the balloon trepan into the interior of the body, in this case, the balloon secured on the distal end of the sleeve of the trepan is placed, folded, around the distal end of the balloon trepan.

Before the operation the balloon is connected with the sleeve of the trepan in such a way that it is possible to inflate it after its insertion into the body. The connection between the sleeve of the trepan and the balloon must therefore be stable with respect to the pressure exerted in inflating it.

In addition, the connection must be secure against slipping. That is, the position of the connection between the sleeve of the trepan and the balloon may not slide either during the instrument's insertion into a body cavity, during the inflating of the balloon, or during removal of the instrument.

During operations a balloon trepan is frequently inserted into the body beyond the balloon's fixing position on the sleeve of the trepan. Therefore it is another requirement that the outer diameter of the balloon trepan must not be substantially increased by means of the method for securing the balloon on the sleeve of the trepan. Otherwise the incision planned for inserting the balloon trepan into the patient's body would have to be unnecessarily increased.

As is explained hereafter, methods are already known for creating a connection between the sleeve of the trepan and the balloon.

The aforementioned U.S. Pat. No. 5,607,443 describes a method for fixing a balloon on the sleeve of a trepan. The distal end of the sleeve of the trepan has an outer and an inner sleeve. The balloon includes a hose-shaped end, which is fixed between the two sleeves by clamping. The hose-shaped end is pressed against a step formed on the inside of the outer sleeve. The step is positioned on the distal end of the outer sleeve; that is, the inner diameter of the outer sleeve is reduced by the step in the direction of its distal aperture. The balloon end is at first pressed around the outside of this step. In the next phase the balloon end is fixed by inserting the inner sleeve into the outer sleeve. On the outside of the inner sleeve a step is formed, which presses the balloon end against the inner step of the outer sleeve.

With this method the installation, especially the insertion of the balloon end into the outer sleeve, requires some practice and is time-consuming. In addition, the inner diameter of the outer sleeve is narrowed by the inserted inner sleeve. The step of the inner sleeve is found outside the outer sleeve. Thus, with a predetermined outer diameter, the space for inserting endoscopes, for instance, is reduced.

In the cited U.S. Pat. No. 5,607,443 another method is described for fixing the balloon on the sleeve of the trepan by means of a hose clamp. A balloon shape often used to equip balloon trepans has a hose-shaped end facing the opening of the balloon. The sleeve of the trepan is inserted into this hose-shaped end. By means of a hose clamp surrounding the hose-shaped end, the balloon is then pressed against the surface of the sleeve of the trepan in order to secure it.

In this manner of securing the balloon, it is a disadvantage that the hose clamp increases the outer diameter of the sleeve of the trepan. Inserting the balloon trepan into the body past the securing site of the balloon on the sleeve of the trepan would thus require a greater incision in the patient's body.

In the German patent DE 298 06 831 U1, an additional method is described for securing the hose-shaped end of the balloon on the sleeve of the trepan. Around the end of the balloon in contact with the sleeve of the trepan a bandage is placed made of non-stretchable material, the ends of which are connected to one another in a contact area, preferably by gluing.

A disadvantage of this method is that faulty installation of the bandage is quite possible. The user must pay attention both to a firm seating of the bandage and also to correct connection of the ends of the bandage in the contact area. Frequent opening and closer of this type of bandage, for instance to correct the seating of the balloon, is not possible as a rule, because this is a one-way product. The tension of the bandage, that is, the force with which the balloon end is pressed against the sleeve of the trepan, can be adjusted during installation only very imprecisely, if at all.

Another known method is to fix the balloon on the sleeve of the trepan by means of an elastic ring. Also with this method, the balloon has a hose-shaped end into which the sleeve of the trepan is inserted. The elastic ring is stretched over the sleeve of the trepan and the end of the balloon. This method is especially problematic when balloons of elastic materials are used. If the hose-shaped end of a balloon secured in this way is made of elastic material, then the elastic ring can be stretched by subjecting the balloon to inner pressure.

If the balloon, or at least the opening of the balloon, consists of elastic material, then there is an additional, already known means of securing a balloon to the sleeve of a trepan. The inner diameter of the balloon opening is configured to be smaller than the outer diameter of the section of the sleeve of the trepan to which the balloon is secured. By means of the elasticity of the balloon material, the diameter can be expanded by stretching in such a way that it becomes possible to slide the balloon up onto the sleeve of the trepan. The differences between the inner diameter of the balloon opening and the outer diameter of the sleeve of the trepan are selected in such a way that the balloon opening rests on the sleeve of the trepan with the desired stability.

This method of installing the balloon is difficult because the balloon can easily be damaged while being slid up onto the sleeve of the trepan. Without additional measures such as, for instance, one of those cited above, this method for the most part is insufficient to provide the required stability of the connection.

It is therefore the object of the invention to provide a balloon trepan which, while avoiding the aforementioned disadvantages, allows the balloon to be secured on the sleeve of the trepan rapidly and securely.

This object is fulfilled by the invention in that the clamping element, by rotating at least one part of the clamping element around a longitudinal axis of the sleeve of the trepan, is movable in the longitudinal direction to the sleeve of the trepan.

The rotation can be transmitted in the longitudinal direction, for instance, by mounting guide curves or threads surrounding the sleeve of the trepan. By rotating at least one part of the clamping element, this element is moved along the guide curve or the thread.

This method has the advantage that the clamping element can easily be brought into every position predetermined, for instance, by the guide curve or by the thread, lengthwise to the sleeve of the trepan.

For instance, it is possible easily to allow a continual sliding of the clamping element in the longitudinal direction of the sleeve of the trepan. This makes it possible to determine at will the power with which the balloon is pressed against the step by the clamping element. Thus, even balloons whose balloon ends are formed in diverse strength can be secured with the desired pressing force, without problem.

In another embodiment of the invention, the clamping element can be fixed on that side of the step on the sleeve of the trepan from which the balloon can be pressed against the step.

With this method the balloon folded over the distal end of the sleeve of the trepan and directed onto the step is fixed as follows. The clamping element is moved into a position in which the balloon is pressed against the step of the sleeve of the trepan. The balloon, when pressed, comes in contact only with a part of the clamping element, while another part of the clamping element serves to fix it on the sleeve of the trepan. The clamping element is fixed in this position on the sleeve of the trepan in such a way that a force is yielded that is sufficient to press the balloon. In special embodiments it is possible to foresee, for instance, that the pressing force of the clamping element is individually adjustable.

The step against which the balloon is pressed can point in the proximal or in the distal direction of the sleeve of the trepan. The clamping element is thus fixed on the proximal or distal side of the step.

This method has the advantage of simplifying error-free fixing of the balloon on the sleeve of the trepan. Because the step formed on the sleeve of the trepan must not necessarily be surrounded by the clamping element, as an additional advantage an enlargement of the inner diameter of the sleeve of the trepan can be achieved while the outer diameter remains uniform.

The clamping element connected with the sleeve of the trepan is guided securely while moving along the sleeve of the trepan to fix the balloon, reducing the chance of faulty operation. It is also possible, for instance, depending on the design, to release it again, easily and reversibly in order to correct the position of the balloon.

In another embodiment of the invention, at least one part of the clamping element is configured in ring-like or tubular shape so that at least one part of its cross-section has an aperture shaped to match the outer cross-section of the sleeve of the trepan.

This method has the advantage that the clamping element can be combined in simple manner with the sleeve of the trepan and at the same time can be configured to be movable in the axial direction. Another advantage of this configuration is that the segment of the balloon end to be clamps does not need to be inserted into the clamping element and laid around its inner side.

In this method the clamping element can be designed, for instance, in such a way that it surrounds the distal end of the sleeve of the trepan in that area that is inserted into the body during an operation and is not surrounded by the balloon. This has the further advantage that this area of the sleeve of the trepan is protected from soiling during the operation. In inserting the distal end of the balloon trepan during an operation, thanks to this method only the balloon and the clamping element are soiled. This reduces the cleansing requirement considerably. Instead of the complete balloon trepan, only the clamping element now needs to be cleaned because the balloon in most cases is exposed only to one-time use. In addition, this makes it possible to configure the relevant part of the clamping element or the complete claming element as a disposable article.

In connection with this method, it can be advantageous for instance that the step is formed by a widening of the outer diameter of the sleeve of the trepan. It can also be advantageous if the outer diameter of the tube-shaped clamping element corresponds to the outer diameter of the expanded segment of the sleeve of the trepan. If the clamping element configured in this way is pushed against the step, then a surrounding fold is formed into which the balloon end can be clamped. It is advantageous that the outer diameter of the sleeve of the trepan is uniform from the distal end all the way past the fixing site of the balloon. There is consequently no projecting part causing a hindrance to inserting the balloon trepan through an incision into a body cavity.

In another embodiment of the invention, the clamping element has a surrounding contact surface which adjoins its surface for the purpose of securing the balloon.

The contact surface can be placed either against the surface of the inside or on the surface of the outside of the balloon.

This method has the advantage that the stability of the connection between the balloon and the sleeve of the trepan is increased and it can more securely resist the pressure during inflation of the balloon. This minimizes the danger, for instance, that during the operation gas or liquid, that is, the medium which is employed for inflating the balloon, can escape from the interior of the balloon into the body cavity.

In an additional embodiment of the invention the contact surface is configured as a front surface of the clamping element.

This method has the advantage that it can be produced with minor expense. The clamping element can be of one-piece design or else composed of several parts. In the direction toward the contact surface, the wall strength of the clamping element can increase in order to allow the configuration of a greater contact surface.

The clamping element can, for instance, also have a ring in such a way that the contact surface is the front surface of the ring. The contact surface can then be formed by the shape of the ring.

In another embodiment of the invention at least one part of the contact surface of the clamping element is inclined against the surface of the sleeve of the trepan.

This method has the advantage that the balloon can be fixed more effectively on the sleeve of the trepan by the clamping element. This method is advantageous, for instance, in combination with the configuration of the invention as described below, in which the border of the balloon opening is configured as a lip. The clamping element and a step inclined vertically or likewise against the surface of the sleeve of the trepan form a ring-shaped hollow area. The lip of the balloon with a corresponding size can be clamped securely into this hollow area.

In an additional embodiment of the invention, at least one part of the step is inclined against the surface of the sleeve of the trepan.

The advantage of this arrangement was already described in the aforementioned embodiment, in that at least one part of the contact surface of the clamping element is inclined against the surface of the sleeve of the trepan. Of course, a combination of these two embodiments is also possible.

In an additional embodiment of the invention the step is mounted so that it can rotate around the longitudinal axis of the sleeve of the trepan.

This arrangement is particularly advantageous in connection with the embodiment in which the clamping element, by rotating at least one part of the clamping element around the longitudinal axis of the sleeve of the trepan, is moved in the longitudinal direction to the sleeve of the trepan. With this embodiment if it is arranged that the entire clamping element, but at least its contact surface, is rotated, then the rotatable mounting of the step, upon firm clamping of the balloon, prevents shearing of the section of the balloon end that is between the contact surface and the step.

The rotatably mounted step can also be fixable in the longitudinal direction to the sleeve of the trepan in order to prevent loss of the latter.

In another embodiment of the invention the clamping element has a handle for its activation.

This arrangement has the advantage that the clamping element can be operated ergonomically on easily recognizable sites.

In another embodiment of the invention the handle is configured as a rotary ring, which by rotating moves the clamping element in the axial direction.

This arrangement has the advantage that the position of the clamping element is ergonomic and can be easily adjusted.

In another embodiment of the invention the handle is mounted on the proximal end of the sleeve of the trepan.

This arrangement has the advantage that the handle must not necessarily be inserted into the body during an operation. It can thus be ergonomic, with greater outer diameter, without causing any disadvantage to the functioning of the balloon trepan. If the handle is mounted in the distal area, which is possibly inserted into the body during an operation, then the handle must be as thin as possible and smoothly configured.

In another embodiment of the invention at least one part of the clamping element is positioned inside the balloon.

This arrangement has the advantage that the clamping element and the balloon can be connected to one another in simple manner before the clamping element is connected with the sleeve of the trepan. The clamping element and the balloon can thus, for instance, be made available as a pre-assembled unit. This unit can be provided as a disposable item.

In another embodiment of the invention the clamping element is moved to secure the balloon in the direction of the proximal end of the sleeve of the trepan.

This movement for closing the clamping element is especially useful when, as in an aforementioned embodiment, at least one part of the clamping element is positioned inside the balloon.

This arrangement has the advantage that the installation of the balloon and the clamping element is further simplified.

In another embodiment of the invention the clamping element is configured as a distal guide of the sleeve of the trepan.

This arrangement has the advantage that the construction of the balloon trepan can be simplified. Because of the reduced number of components, it is easier and less costly to dismantle and clean the sleeve of the trepan.

This arrangement is advantageous when the clamping element configured as a distal guide can be connected with the sleeve of the trepan or inserted into it, in simple manner, for instance through screwing, This makes it possible to connect the balloon, even before installation of the distal guide on the sleeve of the trepan. This considerably facilitates installation of the balloon. The distal guide and the balloon can be made available as a pre-assembled unit and possibly configured as a disposable object. This simplifies cleaning and sterilization of the balloon trepan, because the pre-assembled unit can be produced as pre-sterilized.

The clamping element configured as a distal guide can also be made of transparent material such as transparent plastic. In this way it is easy to observe through an endoscope the cavity to be examined even in the area of the distal guide.

In another embodiment of the invention an opening of the balloon is extended by means of an installation aid, so that the inner diameter of the installation aid is greater than or equal to the outer diameter of the sleeve of the trepan.

Through this arrangement the installation of a balloon whose opening is extended to insert the sleeve of a trepan is made easier. An installation aid is inserted into the opening of the balloon. This aid is, for instance, configured as a tube whose inner diameter is somewhat larger than the outer diameter of the distal end of the sleeve of the trepan. The opening of the balloon can, for instance, be configured as a hose-shaped end. In this case the length of the tube is selected as shorter than the length of the hose-shaped end of the balloon. The extending segment of the hose-shaped end is rolled onto the tube before the installation of the balloon. After inserting the distal end of the sleeve of the trepan into the tube equipped with the balloon up to the site at which the clamping is to take place, the balloon is rolled down. Thereafter its end is situated between the step and the clamping element in such a way that it can be fixed in place by the clamping element. The tube remains in the balloon during the use of the balloon trepan. To prevent any hindrance of sight with an endoscope inserted into the sleeve of the trepan, the tube can be made of a transparent material, for instance a transparent plastic.

It is an advantage of this arrangement that it makes it easily possible to fix a balloon on the sleeve of the trepan by extending the balloon opening. The balloon fixed in this manner can be further secured by any others of the known methods or else by the inventive method. The following possibility is also appropriate, for instance, if the clamping element is fixed on the proximal side of the step. If the opening of the balloon or the hose-shaped end of the balloon through which the sleeve of the trepan is inserted, is selected as smaller than the outer diameter of the distal end of the sleeve of the trepan, then the opening of the balloon during installation, that is in inserting the sleeve of the trepan, was must extended. After passing over the step, the extension of the opening is reduced. Thus, even before closing of the clamping element, the balloon is temporarily fixed on the sleeve of the trepan. If the clamping element is fixed on the distal side of the step, then instead of the step, a similarly configured clamping element can be passed over, for instance during the installation of the balloon, by extending the balloon opening, in order to achieve temporary securing of the balloon.

In another embodiment of the invention, on the rim an opening of the balloon is configured as a lip.

This arrangement has the advantage that the lip can allow a more stable fixing of the balloon end on the sleeve of the trepan. This is especially true when, in the previously described embodiments, the step of the sleeve of the trepan and/or the contact surface of the clamping element is/are inclined against the sleeve of the trepan. On closing the clamping element, thus there results a slit tapering outward. It can be advantageous for securing the balloon if the ring-shaped thickening is found inside this slit. In addition, the balloon end is protected against abrasion by the thickening.

It is evident that the aforementioned traits of the invention and those yet to be explained below can be applied not only in the described combination but also in others without departing from the context of the existing invention.

The invention is more closely described and explained hereafter with the help of some selected embodiments and illustrations.

BRIEF DESCRIPTION OF THE ILLUSTRATIONS

DETAILED DESCRIPTION OF DRAWINGS

Figure 1:
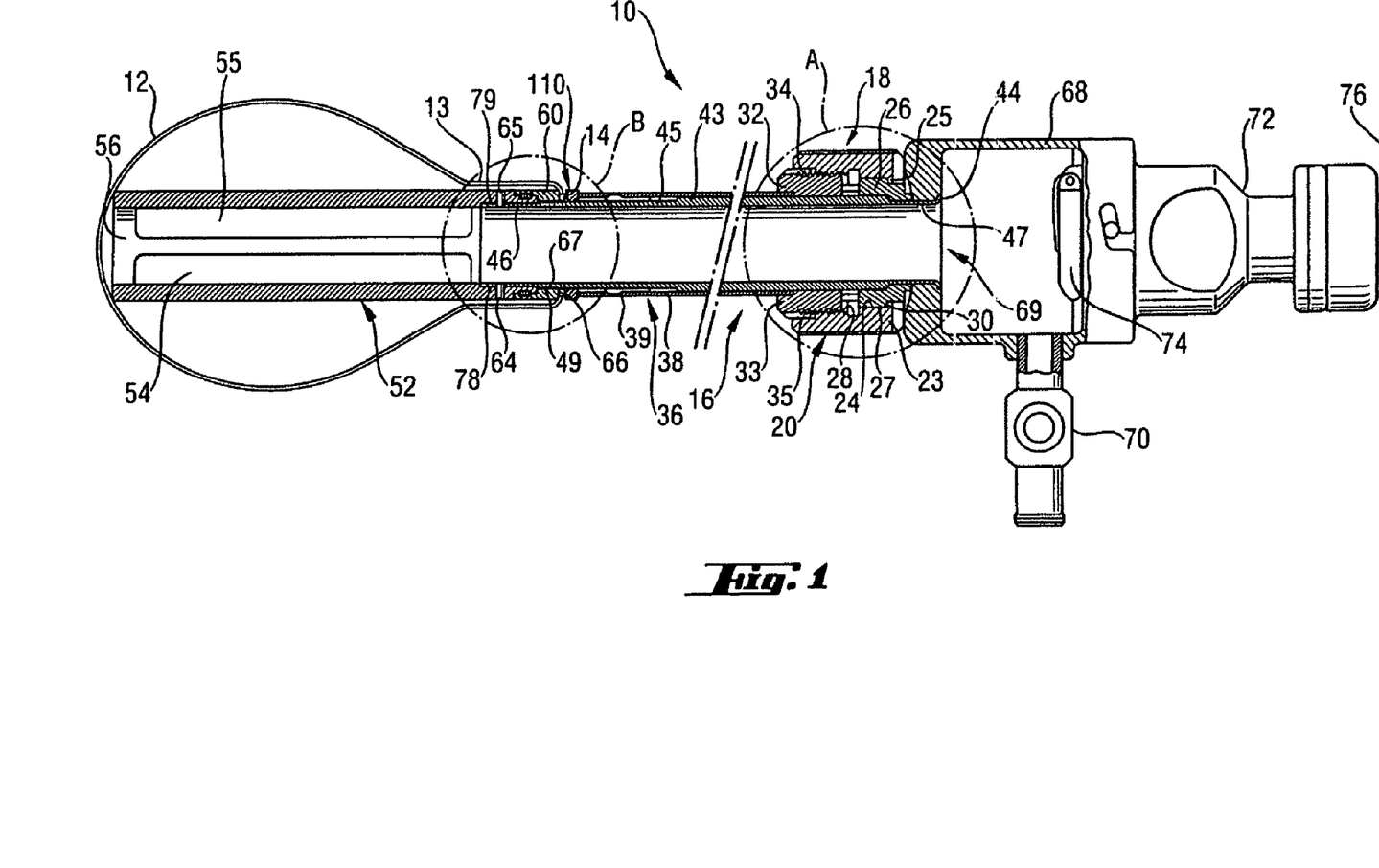
FIG. 1 shows a side view, partly cut away in the longitudinal section, of an inventive balloon trepan according to a first embodiment.
Figure 1A:
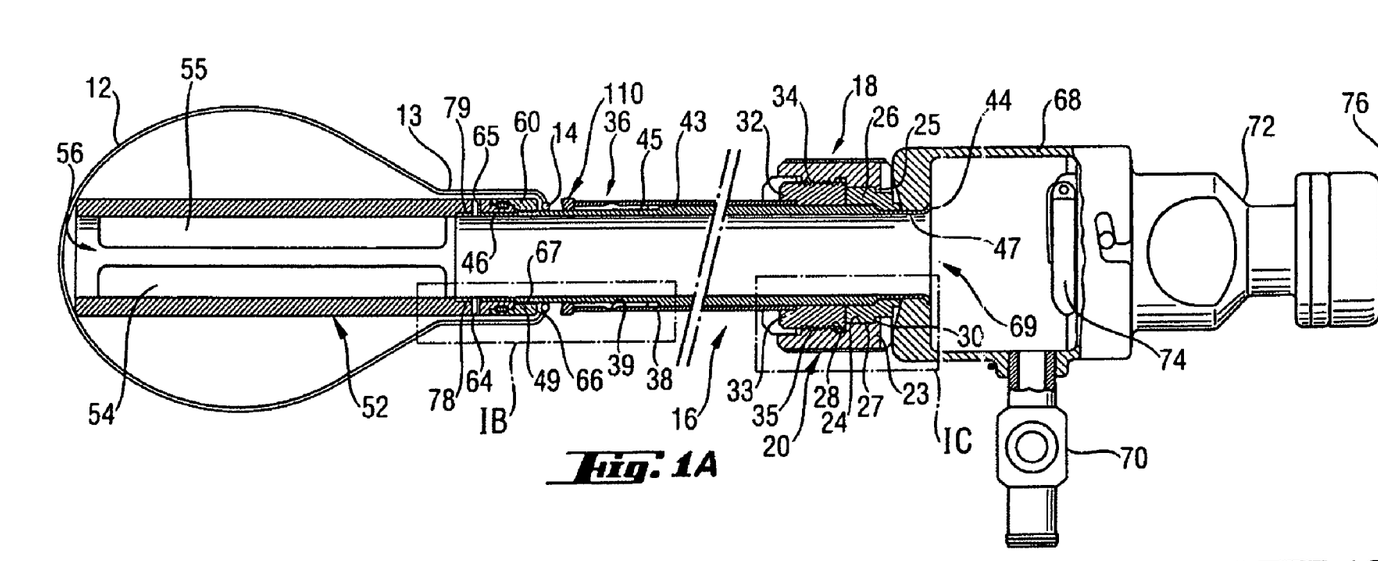
FIG. 1A shows a depiction according to FIG. 1 with opened clamping element.

A balloon trepan 10 of a first embodiment consisting of a balloon 12 and a sleeve of a trepan 16 is seen in FIGS. 1 and 1A in longitudinal section. The balloon 12 on the opening has a lip 14 configured as a ring-shaped thickening, which is fixed by means of the clamping element 18 on the balloon trepan 10.

The balloon 12 is made of a silicon-based elastic material, which is transparent when stretched. The balloon 12, extending from the lip 14, has a hose-shaped section 13, followed by a teardrop-shaped balloon body that is not designated in more detail.

Figure 2:
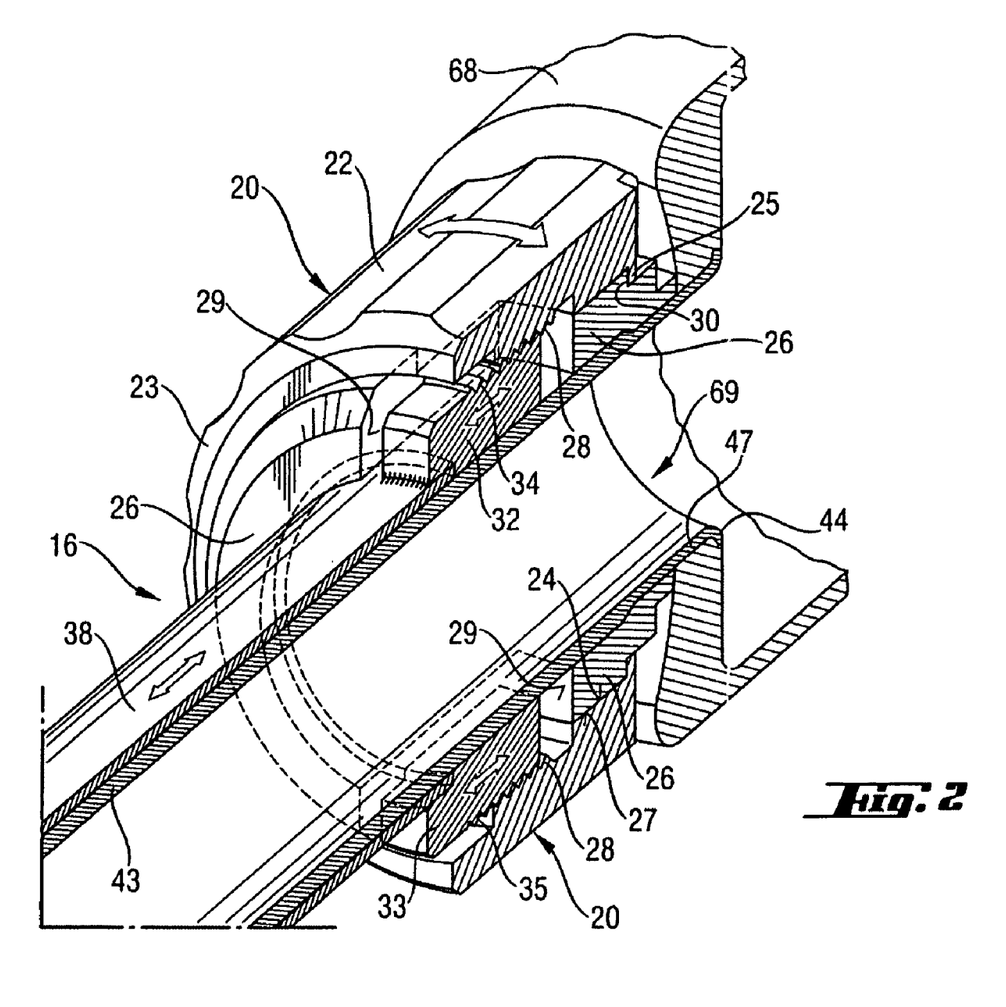
FIG. 2 shows an enlargement of the section of FIG. 1 designated as A in perspective view.
Figures 3, 4:
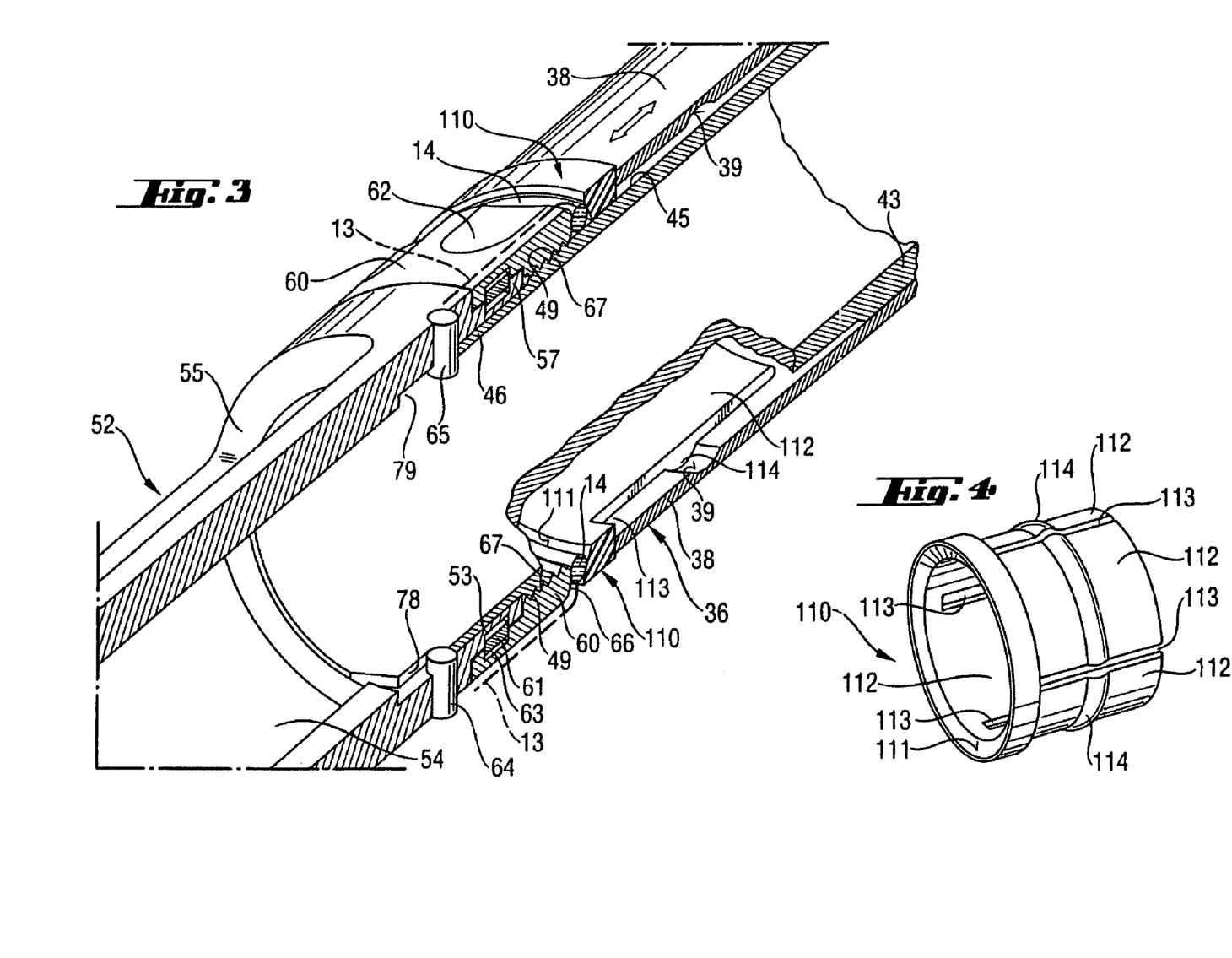
FIG. 3 shows an enlargement of the section of FIG. 1 designated as B in perspective view; instead of the complete balloon, only its lip with indicated hose-shaped section shown.
FIG. 4 shows a perspective view of an inventive component of the clamping element according to the first embodiment.

FIGS. 2 and 3 show enlarged perspective views of the sections of FIG. 1 designated as A and B.

The handle 20 and sleeve 36 are parts of the clamping element 18. The clamping 18, as shown in FIG. 1 and partly in FIG. 2, is moved in axial direction by activation of a handle 20. The handle 20 has a rotary ring 23, which is positioned rotatably on a mount 26, which mount surrounds the main sleeve 43 of the sleeve of the trepan 16 and is connected with the sleeve by a soldered joint.

Sliding the rotary ring 23 in the longitudinal direction to the proximal end is prevented by a valve body 68. Sliding in this direction is restricted by the shoulder 25 of the rotary ring 23 and the step 30 of the mount 26.

The main sleeve 43 and valve body 68 are connected to one another through a positive coupling. The diameter of the opening 69 of the valve body 68 corresponds in the distal area of the opening 69 with the outer diameter of the main sleeve 43. In the proximal area the diameter of the opening 69 is widened. The valve body 68 is fixed in the distal direction by the mount 26 and in the proximal direction by the rim 44 of the main sleeve 43 edged up, according to the widened inner diameter of the opening 69, outward. The main sleeve 43 has on its proximal end a tapering 47 of the outer diameter. Because the inner diameter of the main sleeve 43 remains uniform, a reduction of the wall strength is achieved, which makes possible the edging up of the rim 44.

The mount 26 has a surrounding sliding surface 27, which on the proximal side is restricted by a step 30. The outer diameter of the mount 26 in the area of the sliding surface 27 corresponds to the inner diameter in the area of the sliding surface 24 of the rotary ring 23.

In the rotary 23 an inner thread 28 is configured, through which the transported elements 32 and 33 are moved along the sleeve of the trepan 16 upon rotation of the rotary ring 23. The shape of the transported elements 32 and 33 can be described as a segment of a ring surrounding the sleeve of the trepan. These transported elements 32 and 33 are mounted on opposite sides around the sleeve of the trepan 16 between the outer surface of the outer tube 38 and the inner side of the rotary ring 23. On the outside the transported elements have thread segments 34 and 35 which engage in the inner thread 28 of the rotary ring 23. The transported elements 32 and 33 are connected with the outer tube 38 of the sleeve 36.

The outer tube 38 surrounds the area of the sleeve of the trepan between the handle 20 mounted on the proximal side and the balloon 12. The outer tube 38 and the ring 110 form the sleeve 36.

The transported elements 32 and 33 move in the direction of the longitudinal axis of the sleeve of the trepan 16 in notches of the mount 26. One of the two notches is shown in FIG. 2 and designated with reference number 29. Turning the rotary ring 23 produces a movement of the sleeve 36 in the longitudinal direction, without the sleeve 36 itself being turned.

To make handling easier, as shown in FIG. 2, several troughs are configured on the outside of the rotary ring 2, which prevent slipping when the ring is activated. One trough is designated, in exemplary manner, with the reference number 22 (FIG. 2).

Figure 1B:
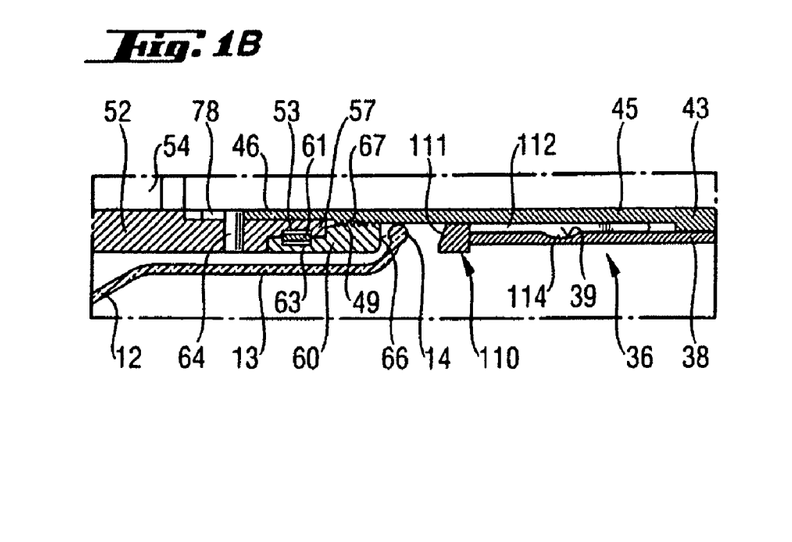
FIG. 1B shows an enlargement of the section of FIG. 1A designated as IB.
Figure 1C:
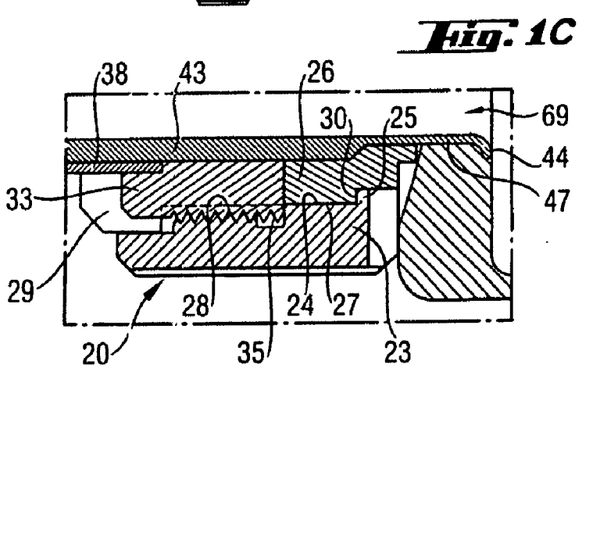
FIG. 1C shows an enlargement of the section of FIG. 1A designated as IC.

The contact surface 111 (FIGS. 1B and 3) of the clamping element 18, which is in contact with the surface of the balloon 12 to secure it, is a part of the ring 110.

FIG. 4 shows a perspective view of the ring 110. The front surface of the ring 110 serves as contact surface 111, which can be pressed to secure the balloon against its surface. The contact surface 111 is inclined against the surface of the sleeve of the trepan 16.

The four strips of the ring 110, which are designated as number 112 in their entirety (FIG. 4), grip between the outside of the main sleeve 43 and the inside of the outer tube 38. The strips 112 are separated from one another by the notches, which are designated in their entirety as number 113. The interval required to include the strips 112 is produced by the tapering 45 of the outer diameter of the main sleeve 43 (FIG. 3).

The protuberances surrounding the outsides of the strips, designated in their entirety as number 11, mesh to axially fix the ring 110 into the ring groove 39, which is configured on the inside of the outer tube 38. The strips 112 are elastic so that when the ring 110 is mounted, they can be arched inward to engage the protuberances 114 in the ring groove 39. The ring 110 is made of plastic and, in another embodiment of steel.

The step 66, against which the balloon 12 is pressed by the clamping element 18, is, as shown in FIG. 1, a part of the stapling ring 60. This ring serves at the same time to secure the cage 52 on the main sleeve 43. The stapling ring 60 is connected so that it rotates with the cage 52. This connection is provided by a spring ring 61 (FIG. 3), which is positioned both in the groove 53 surrounding the outside of the cage 52 and in the groove 63 worked into the inside of the stapling ring 60.

To secure the cage 52 by the stapling ring 60 on the main sleeve 43, as seen in FIG. 3, the stapling ring 60 is firmly screwed by the inner thread 67 and the outer threat 49 on the main sleeve 43. On the outside of the stapling ring 60, troughs 62 are configured in order to facilitate its operation.

In the area of the distal end 46 of the main sleeve 43, which extends into the cage 52, the outer diameter is further reduced in comparison with the tapering 45. The inner diameter of the cage 52 is widened on its proximal end, so that it receives the distal end 46 of the main sleeve 43 precisely. The inner diameter of the entire sleeve of the trepan 16 is uniform.

The cage 52, as shown in FIGS. 1 and 3, is secured against rotation by the positioning rods 64 and 65. These rods are mounted on the cage 52 in such a way that they extend into its interior. If the cage 52 is secured on the main sleeve 43, the positioning rods 64 and 65 extend into the notches 78 and 79 of the main sleeve 43.

The cage 52 has four openings surrounding it, two of which are shown in the illustrations, designated with reference numbers 54 and 55. These openings and the opening 56 on the distal end of the cage 52 serve to observe with an endoscope inserted into the sleeve of the trepan 16, but not shown in the illustrations.

The valve body 68, as shown in FIGS. 1 and 1A, is equipped with a valve flap 74. An inlet 72 is connected with the valve body 68. The proximal opening 76 of the inlet 72 serves to insert a (not illustrated) endoscope. A flush-intake 70 mounted on the valve body 68 serves to inflate the balloon with a liquid or with a gas, or to empty it.

To install the balloon the hose-shaped section 13 of the balloon 12 is folded over the cage 52 and the stapling ring 60. With the clamping element 18 opened, the lip 14 of the balloon 12 is mounted on the proximal side on the step 66, so that the lip 14 surrounds the tapering 45 of the main sleeve 43 and at the same time is in contact with the step 66 (FIG. 1A). The inner diameter of the hose-shaped section 13 and of the lip 14 is, with the material loosened, smaller than the outer diameter of the cage 52, of the stapling ring 60, and of the tapering 45. For purposes of installation, the hose-shaped section 13 and the lip 14 must thus be stretched. After passing over the step 66, the stretching is reduced again. Thus, even before closing the clamping element 18, the balloon 12 is temporarily secured against slipping. By turning the rotary ring 23, the clamping element 18 is moved into the closed position; that is, the lip 14 is clamped in with the desired force between the step 66 and the contact surface 111 of the ring 110 (FIG. 1).

Figure 5:
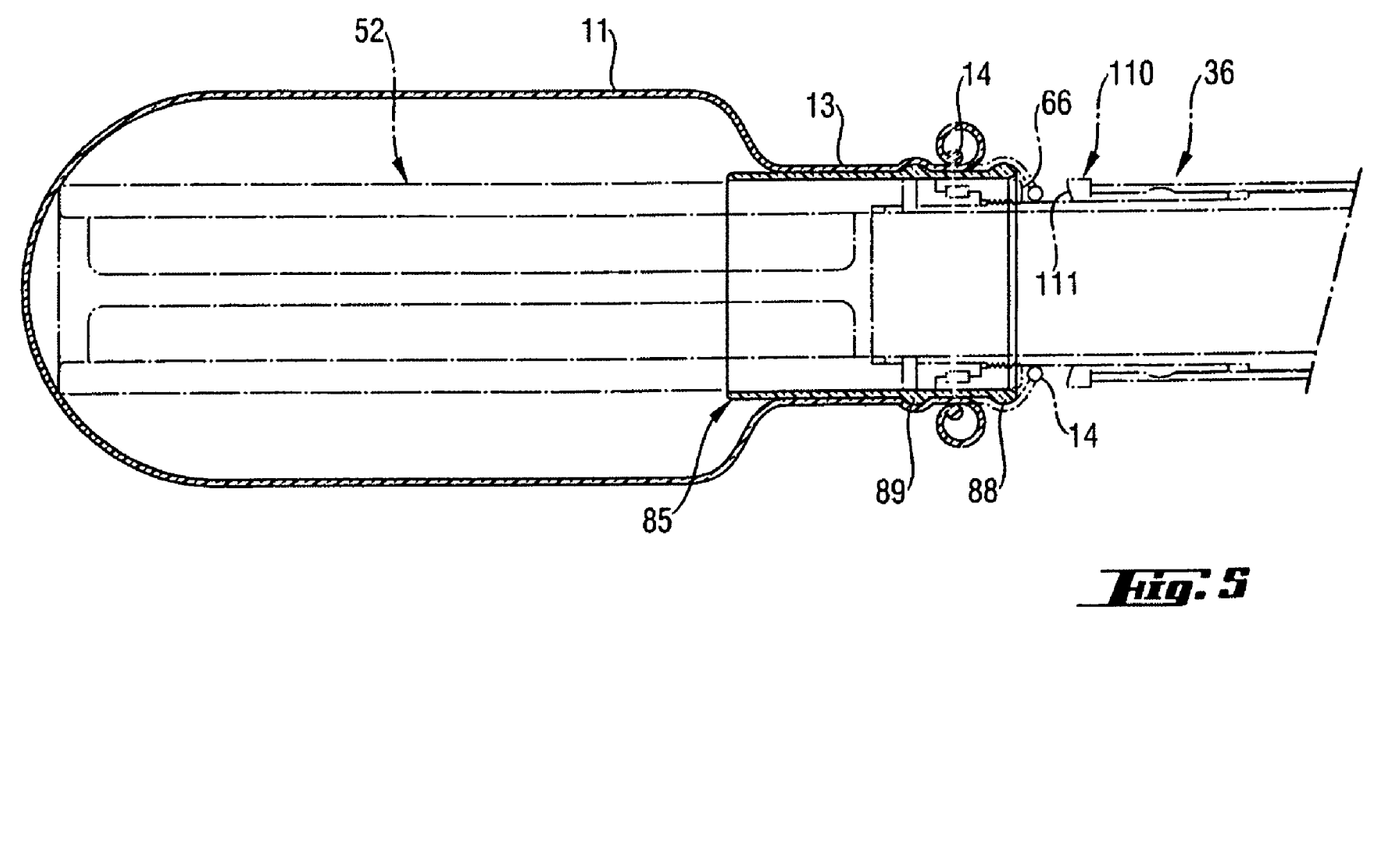
FIG. 5 shows a longitudinal section of an inventive balloon with installation aid according to the second embodiment.

In a second embodiment the balloon 11, as seen in longitudinal section in FIG. 5, is equipped with an installation aid 85. The installation aid 85 consists of a tube of transparent plastic, whose inner diameter is somewhat larger than the outer diameter of the cage 52 and of the stapling ring 60. The installation aid 85 is shorter than the hose-shaped section 13 of the balloon 11. The inner diameter of the hose-shaped end 13 is smaller than the outer diameter of the installation aid 85. The installation aid 85 thus stretches the hose-shaped section 13. The part of the hose-shaped section 13 extending outward to open is rolled onto the outside of the installation aid before installation. Surrounding protuberances 87 and 88 on the surface of the installation aid 85 prevent unwanted rolling of the rolled-up section of the hose-shaped section 13.

The balloon 111 of the second embodiment is of similar construction as the balloon 12 of the first embodiment. The teardrop-shaped balloon body was replaced, however, by a longer, cylindrical one.

In a third embodiment the structure of the balloon trepan is modified on the distal side of the valve body.

Figure 8:
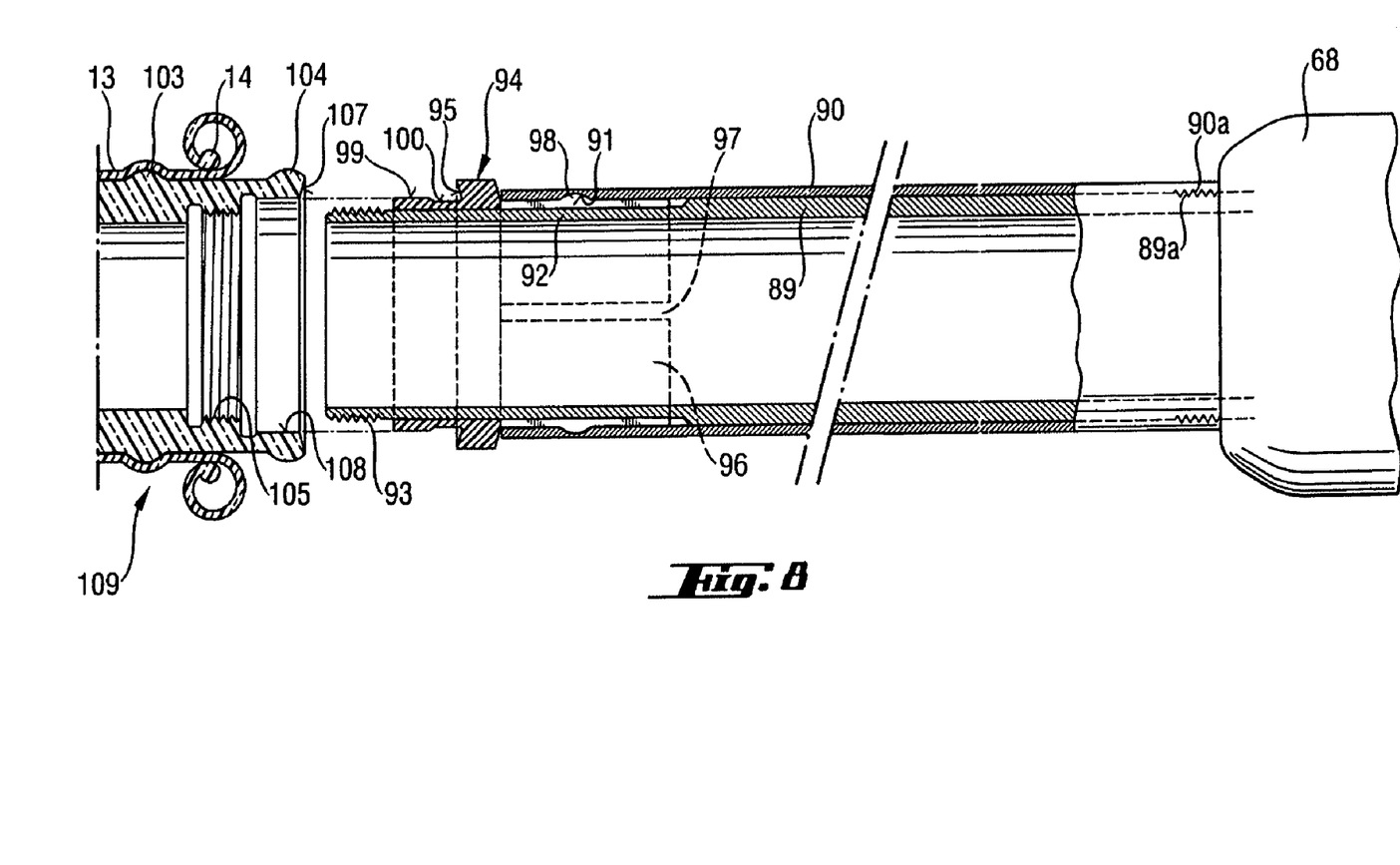
FIG. 8 shows a portion of a side view, partly in cut away longitudinal section, of an inventive sleeve of a trepan according to the third embodiment.

FIG. 8 shows the section, partly opened up in a longitudinal section, of a side view of a sleeve of a trepan 15 according to the third embodiment. The main sleeve 89, like the main sleeve 43 of the first and second embodiments, is connected with the valve body 68. The outer tube 90 surrounds the main sleeve 89 of the valve body 68 as far as the ring 94, which is connected with the outer tube 90. The ring 94 forms the step 95, against which the lip 14 of the balloon 10 can be pressed in order to secure it.

The outer tube 90 and the main sleeve 89 are screwed together on the proximal end of the main sleeve 89 by an outer thread 89a on the outside of the main sleeve 89 and an inner thread 90a on the inside of the outer tube 90.

Figures 6, 7:
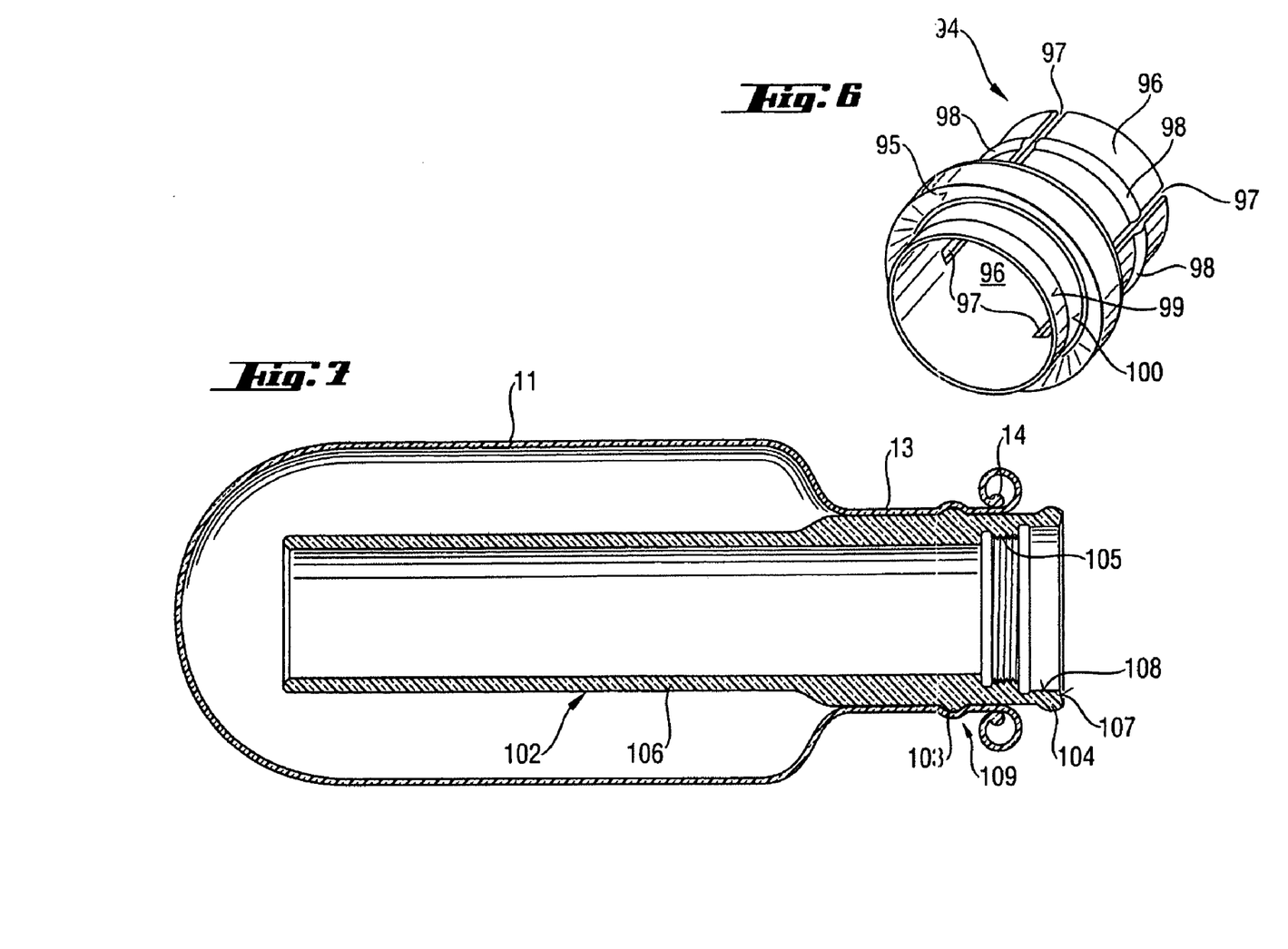
FIG. 6 shows a perspective view of an inventive component of the clamping element according to a third embodiment.
FIG. 7 shows a longitudinal section of an inventive balloon with distal guide according to the third embodiment.

The clamping element 102, as shown in FIG. 7, is configured as a distal guide. This element is screwed onto the main sleeve 89 by its inner thread 105 and the outer thread 93 mounted on the distal end of the main sleeve 89 seen in FIG. 8. The lip 14 of a balloon 11 to be secured is pressed against the step 95 by the contact surface 107 of the clamping element 102. The contact surface 107 is inclined against the surface of the sleeve of the trepan 15. The pressing force can be adjusted by turning the clamping element 102.

The clamping element 102, as shown in FIG. 7, is of one-piece transparent plastic construction. In the distal area 106, the outer diameter of the clamping element 102 is reduced. The transparent material makes possible observation with an endoscope inserted into the sleeve of the trepan. The pre-assembled unit consisting of clamping element 2 and balloon 11 is produced as a disposable product.

The inner diameter of the hose-shaped section 13 of the balloon 11 is smaller than the outer diameter of the proximal area 109 of the clamping element 102. In installing the balloon 11 in the proximal area 109, the hose-shaped section 13 is thus stretched. The part of the hose-shaped section 13 extending out to the opening is rolled up onto the outside of the clamping element 102 before it is screwed on. Two ring-shaped protuberances 103 and 105 on the surface of the proximal area 109 prevent unwanted rolling of the rolled-up section of the hose-shaped section 13.

The step 95, against which the lip 14 of the balloon 11 is pressed by the clamping element, is part of the ring 94. The step 95 is inclined against the surface of the sleeve of the trepan 15.

FIG. 6 shows a perspective view of the ring 94. As already described in the first embodiment with the securing of the ring 110 on the outer tube 38, four strips of the ring 94, designated in their entirety as 96, grip between the outside of the main sleeve 89 and the inside of the outer tube 90. The strips 96 are separated from one another by the notches 97, which in their entirety are designated as 96. The intervening space required for the strips 96 is provided by the tapering 92 of the outer diameter of the main sleeve 89.

The protuberances surrounding the outside of the strips, which in their entirety are designated with reference number 98, grip into the ring groove 91, which is configured on the inside of the outer tube 90, to secure the ring, as described in the first embodiment. The ring 94 is thus mounted in the main sleeve 89 so that it can rotate around the longitudinal axis of the sleeve of the trepan.

The ring 94 has a support 99 in the distal direction, which connects to the step 95. The support 99 has a surrounding indentation 100, connecting directly to the step 95 as seen in FIGS. 6 and 8. The ring 94 is, like ring 110, made of plastic or steel.

If the clamping element 102 is mounted on the main sleeve 89, the support 99 extends into the opening 108 of the clamping element 102.

By rolling out the rolled-up section of the hose-shaped section 13, it is thus possible to ensure that the lip 14 of the balloon 12 comes to rest against the support 99. The firm clamping of the lip 14 occurs through rotation of the clamping element 102. The support 99 makes it possible that, during the firm clamping of the lip 14, the clamping element 102 can make the rotation movement. Damage to the lip 12 by shearing force is thus avoided. Upon firm clamping along the support 99, the lip 12 is pushed until it engages in the indentation 100 and until the desired pressing force is achieved.

What is claimed is:

1. A balloon trepan, comprising:
   a sleeve of the trepan;
   a balloon which removeably surrounds a distal end of the sleeve of the trepan, so that the balloon can be pressed against a peripheral step formed on the sleeve of the trepan to fix it to the sleeve of the trepan; and
   a clamping element movable in a longitudinal direction along said sleeve to press said balloon against the peripheral step, said clamping element displaced in the longitudinal direction along said sleeve by rotation of at least one part of the clamping element about a longitudinal axis of the sleeve of the trepan.

2. A balloon trepan according to claim 1, distinguished in that the clamping element on one side of the step can be secured onto the sleeve of the trepan, by which the balloon can be pressed against the step.

3. A balloon trepan according to claim 1, distinguished in that at least one part of the clamping element is one of a group consisting of ring-shaped or tubular in configuration, and at least one part of its cross-section has an aperture corresponding in shape to the outer cross-section of the sleeve of the trepan.

4. A balloon trepan according to claim 1, distinguished in that the clamping element has a peripheral contact surface which is in contact with a contact surface of the balloon in order to fix said balloon to the peripheral contact surface.

5. A balloon trepan according to claim 4, distinguished in that the peripheral contact surface is configured as a front surface of the clamping element.

6. A balloon trepan according to claim 4, distinguished in that at least one part of the peripheral contact surface of the clamping element is inclined against the surface of the sleeve of the trepan.

7. A balloon trepan according to claim 1, distinguished in that at least one part of the step is inclined against the surface of the sleeve of the trepan.

8. A balloon trepan according to claim 1, distinguished in that the step is mounted so that it can rotate around the longitudinal axis of the sleeve of the trepan.

9. A balloon trepan according to claim 1, distinguished in that the clamping element has a handle in order to activate it.

10. A balloon trepan according to claim 9, distinguished in that the handle is configured as a rotary ring, which by turning moves the clamping element in the axial direction.

11. A balloon trepan according to claim 9, distinguished in that the handle is mounted on the proximal end of the sleeve of the trepan.

12. A balloon trepan according to claim 1, distinguished in that at least one part of the clamping element is positioned inside the balloon.

13. A balloon trepan according to claim 1, distinguished in that the clamping element is moved in the direction of the proximal end of the sleeve of the trepan in order to fix the balloon.

14. A balloon trepan according to claim 1, distinguished in that the clamping element is configured as a distal guide of the sleeve of the trepan.

15. A balloon trepan according to claim 1, distinguished in that an opening of the balloon is extended by means of an installation aid so that the inner diameter of the installation aid is greater than or equal to the outer diameter of the sleeve of the trepan.

16. A balloon trepan according to claim 1, distinguished in that a border of an opening of the balloon is configured as a lip.

17. A balloon trepan according to claim 1, wherein the at least one part of the clamping element is a rotary ring, which by turning moves the clamping element in the axial direction, wherein said rotary ring is fixed about the sleeve in the longitudinal direction.

* * * * *